United States Patent [19]

Wymer et al.

[11] 4,279,628
[45] Jul. 21, 1981

[54] APPARATUS FOR DRYING A NATURAL GAS STREAM

[75] Inventors: Robert L. Wymer, Poland, Ohio; Perry Prater, Shreveport, La.

[73] Assignee: Energy Synergistics, Inc., Daingerfield, Tex.

[21] Appl. No.: 108,504

[22] Filed: Dec. 31, 1979

[51] Int. Cl.³ .......................................... B01D 53/18
[52] U.S. Cl. .................................. 55/238; 55/29; 55/48; 55/89; 261/115
[58] Field of Search .............. 55/29, 31, 32, 48, 55, 55/89, 238; 261/115, 116, 118

[56] References Cited

U.S. PATENT DOCUMENTS

| | | | |
|---|---|---|---|
| 1,564,052 | 12/1925 | Ehrhart | 261/118 |
| 2,230,088 | 1/1941 | Podbielniak | 55/32 X |
| 2,564,583 | 8/1951 | Sebald | 261/115 |
| 2,604,185 | 7/1952 | Johnstone et al. | 55/238 X |
| 3,322,411 | 5/1967 | Moore | 55/32 X |
| 3,403,522 | 10/1968 | Henry | 55/31 X |
| 3,624,985 | 12/1971 | Giles | 261/118 X |
| 3,634,998 | 1/1972 | Patterson | 55/32 |
| 3,780,499 | 12/1973 | Dorr et al. | 55/32 |
| 3,912,469 | 10/1975 | Ewan et al. | 55/238 |
| 4,073,832 | 2/1978 | McGann | 261/118 |
| 4,188,368 | 2/1980 | Wolf et al. | 261/118 X |

*Primary Examiner*—Robert H. Spitzer
*Attorney, Agent, or Firm*—Webster B. Harpman

[57] ABSTRACT

An improved method and apparatus for drying a natural gas stream such as water containing natural gas introduces triethylene glycol into a high speed gas stream at a pressure in excess of that of the gas stream to achieve a drying effect by impaction and rapid expansion and turbulence in a mixing zone. The triethylene glycol and water are removed by a centrifugal separator.

5 Claims, 6 Drawing Figures

APPARATUS FOR DRYING A NATURAL GAS STREAM

BACKGROUND OF THE INVENTION (1) Field of the Invention

This invention relates to drying natural gas by removing water and/or sulfur compounds from wells, transmission lines, gathering stations, and the like.

(2) Description of the Prior Art

Apparatus and methods heretofore used for drying natural gas are generally concerned with the exposure of the moisture carrying gas to trays of glycol such as illustrated for example in U.S. Pat. No. 4,070,231.

Similar devices are found in U.S. Pat. No. 3,664,091 and are referred to in U.S. Pat. Nos. 3,864,103 and 4,010,009.

A somewhat different device for removing water from natural gas may be seen in U.S. Pat. No. 3,322,411 wherein a generally horizontally disposed fluid flow passage is filled with a porous material, wet gases directed therethrough and glycol is introduced at intervals therealong.

The prior art devices are usually of fixed design and related in size to the particular flow volume of a gas well and the prior art units are generally unable to remove water and contaminants from the gas stream beyond the point of equlibrium in that they cannot remove more water than the glycol is able to absorb.

The present invention will remove water beyond the point of equilibrium due to the injection of the triethylene glycol into the high speed gas stream and the arrangement which permits an expansion in a turbulent flow in a mixing zone with the resulting extremely high surface to mass ratio and a resulting high degree of interpenetration of water and glycol.

Additionally the apparatus and method result in the cooling of the gas stream in a refrigeration and change of pressure effect, all of which contribute to a superior drying action.

The present method and apparatus can be varied to match various flow volumes and pressures by merely changing the triethylene glycol injection nozzles thus rendering the invention readily adaptable to many situations.

SUMMARY OF THE INVENTION

An apparatus and a method for drying a natural gas stream is disclosed which directs the wet natural gas through a nozzle to form a jet stream and introduces triethylene glycol into the jet stream at a pressure in excess thereof and provides for a turbulent flow in a mixing zone which also permits rapid expansion so that the fluids are divided into many tiny particles with an extremely high surface to mass ratio so as to provide a high degree of interpenetration of the water and triethylene glycol. The triethylene glycol collects water upon contact and the considerably greater contact realized with the present apparatus and method results in an extremely high efficiency. The fluid mixture leaves the mixing zone and the water glycol mixture is spun out in a centrifugal spin chamber with the water and glycol mixture being removed at the bottom of the separator. The glycol water mixture is subsequently fed through a standard glycol regenerating (stripping) station where the glycol is stripped of the water and returned to the process and apparatus and the water drained away.

DESCRIPTION OF THE PREFERRED EMBODIMENT

Figure 1:
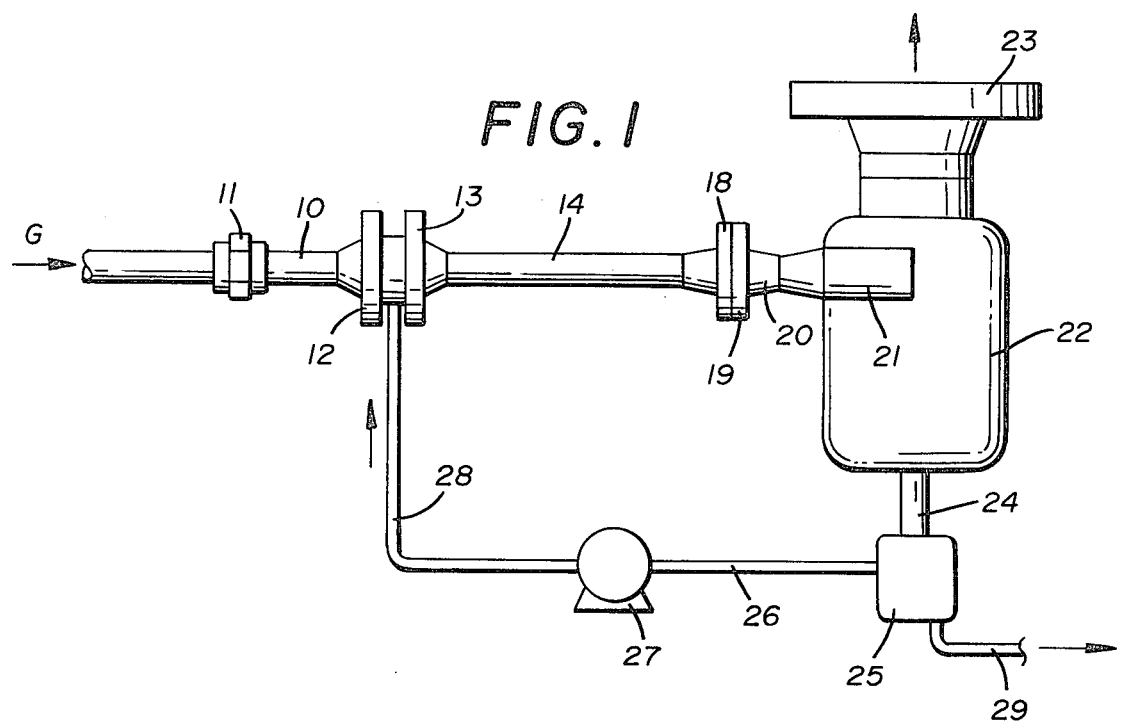
FIG. 1 is a diagrammatic view of the improved apparatus of the invention.

In the form of the invention chosen for illustration and description herein, the apparatus and method for drying a natural gas stream is best seen in FIG. 1 of the drawings which is a diagrammatic disclosure in which natural gas from a well or collecting main is introduced into the device at the left thereof as indicated by the arrow and the letter G. The introduction is by way of an adaptor 10, one end of which is engaged in a coupling 11 by which communication is established with the natural gas supply line and the other end is flanged at 12 and secured to a flange 13 on a tubular mixing member 14.

Figure 2:
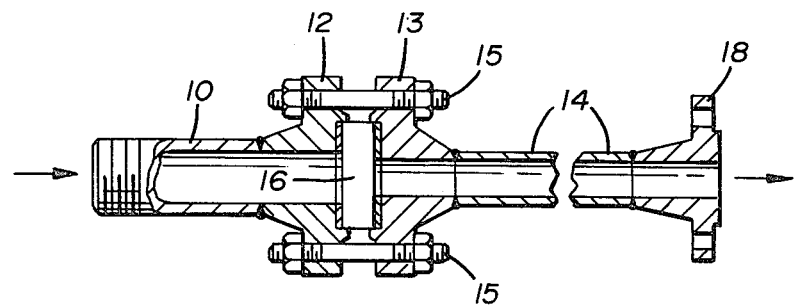
FIG. 2 is an enlarged cross sectional detail of a portion of the apparatus seen in FIG. 1 with parts broken away.
Figure 4:
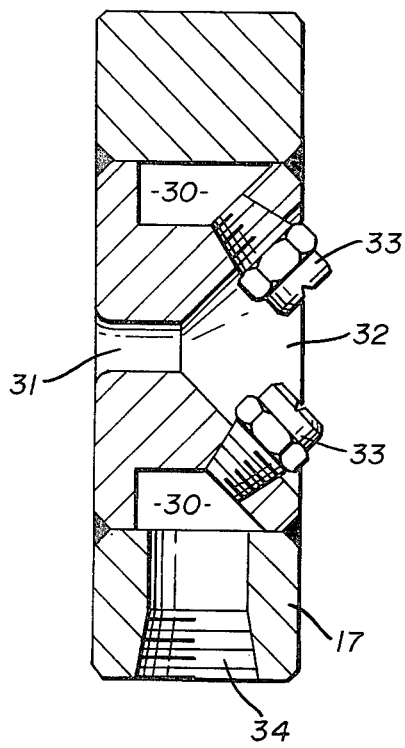
FIG. 4 is an enlarged detail in vertical section showing a glycol injecting nozzle used in the apparatus illustrated in FIGS. 1 and 2.

In FIG. 2 of the drawings, the adaptor 10 and the tubular mixing member 14 are shown with the flanges 12 and 13 secured to one another by bolt and nut fasteners 15 and it will be observed that the configuration of the flanged ends 12 and 13 is such that a nozzle chamber 16 is defined therebetween. The nozzle 17 in FIGS. 4 and 5 of the drawings is normally positioned in the nozzle chamber 16.

Figure 3:
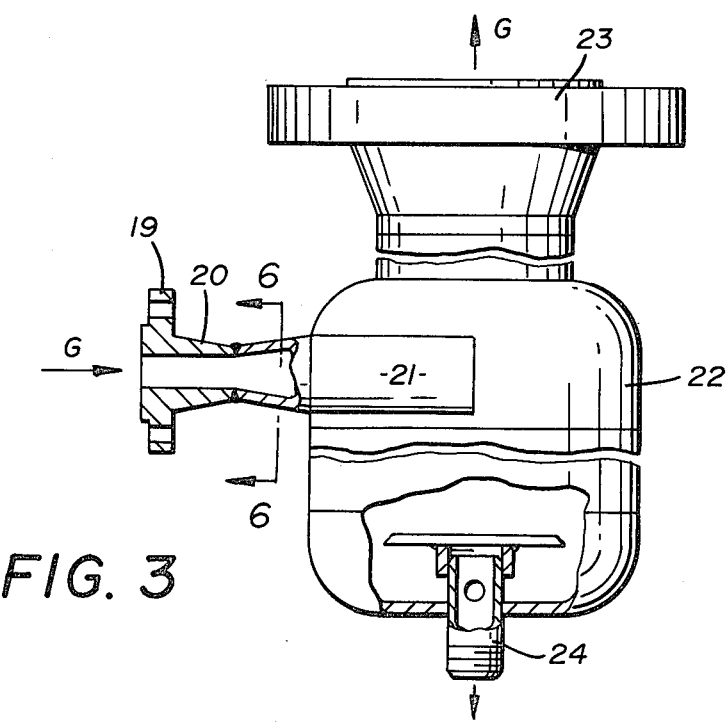
FIG. 3 is an enlarged detail of a centrifugal separator seen in FIG. 1 of the drawings with parts broken away and parts in cross section.
Figure 6:
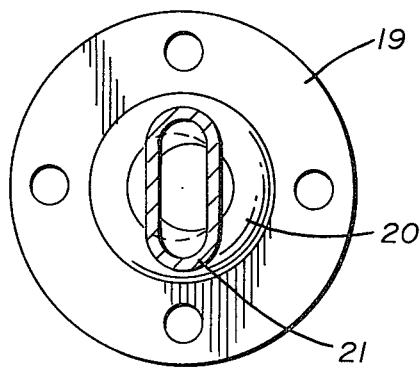
FIG. 6 is a cross sectional detail on lines 6—6 of FIG. 3.

By again referring to FIG. 1 of the drawings, it will be seen that the opposite end of the tubular mixing member 14 with respect to the flange 13 is flanged as at 18 and joined thereby to a flange 19 on a transition section 20 which is circular at its point of engagement with the flange 19 and oval at its opposite end 21 where it tangentially joins a centrifugal separator 22 as may be seen by referring to FIGS. 3 and 6 of the drawings.

In FIG. 3 of the drawings, the water and glycol are separated from the natural gas by the cyclone created by the centrifugal spin due to the tangential introduction of the fluids thereinto, the dry gas flows outwardly upwardly through the open upper end 23 of the centrifugal separator 22 and the glycol and water flow downwardly and out of the centrifugal separator 22 by way of a drain line 24.

By referring again to FIG. 1 of the drawings, it will be seen that the drain line 24 communicates with a conventional stripping station 25 as known in the art in which the glycol is separated from the water and delivered to a tube 26 which communicates with a pump 27 which in turn communicates with the glycol injecting nozzle 17 by way of a tube 28. The water leaves the stripping station by a drain line 29.

As heretofore mentioned, the injection of the triethylene glycol into the jet stream of natural gas is occasioned by a nozzle assembly 17 which is normally disposed in the nozzle chamber 16 as best seen in FIG. 2 of the drawings. The nozzle assembly is illustrated in enlarged detail in FIGS. 4 and 5 of the drawings and by referring thereto it will be seen that the nozzle assembly body 17 has an annular chamber 30 therein which surrounds a jet forming opening 31 through which the natural gas to be dried is directed. The jet forming opening 31 is of substantially smaller diameter than the internal diameter of said adaptor 10. The downstream end of the jet opening 31 communicates with a conical chamber 32 and a plurality of individual glycol injection nozzles 33 are arranged in a circumferential pattern in the conical chamber 32 so as to communicate with the annular chamber 30 hereinbefore described. A drilled and tapped opening 34 communicates with the annular chamber 30 and with the tube 28 as seen in FIG. 1 of the drawings so that dry triethylene glycol delivered by the pump 27 through the tube 28 will be supplied in suitable volume and at a pressure in excess of the pressure of the natural gas emerging from the jet opening 31 and thereby delivered into the jet stream of the natural gas so as to cause a turbulent mixing action therein. If necessary more than one of the drilled and tapped openings 34 are provided so as to insure an adequate supply of glycol to the device.

Figure 5:
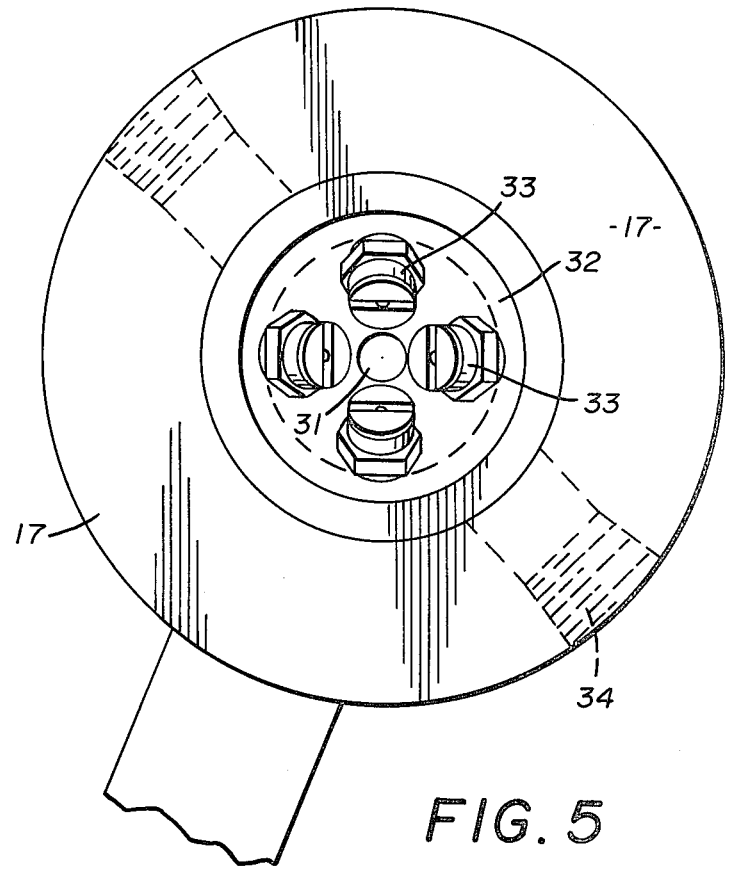
FIG. 5 is a plan view of the glycol injecting nozzle seen in FIG. 4.

In FIG. 5 of the drawings, the circumferential arrangement of the individual glycol injecting nozzles 33 will be seen and it will be observed that the nozzles 33 are positioned at uniform angles from the horizontal center line of the jet opening 31 and so that the triethylene glycol introduced through the relatively small openings of the individual glycol nozzles 33 will impinge in and intermix in the gas stream in the tubular mixing member 14 and that portion thereof surrounded by the flange 13 as heretofore referred to.

It will thus be seen that the apparatus and method disclosed herein for drying a natural gas stream uses chemicals plus pressure and cooling in a synergistic effect with the inter-reacting forces acting effectively due to the re-expansion of the fluids in the mixing member 14 and the simultaneous tubulent flow generated by the rapid expansion and the resulting high degree of interpenetration and cooling at the point of mixing which results in an extremely efficient water removal.

As will be understood by those skilled in the art, the triethylene glycol collects water upon contact and thus the greater the contact the higher the collection efficiency. The gas jet created and controlled in the apparatus and upon which the method depends, provides sufficient energy for the centrifugal separation of the water and glycol from the gas in the centrifugal separator 22 and the additional expansion area thereof slows down the gas stream and insures against its retention of any of the liquids, which as hereinbefore explained are drained away through the bottom of the centrifugal separator 22.

The method realized by the apparatus thus depends primarily upon the degree of atomization of the triethylene glycol, the high speed contact thereof, and the massive mixing of water and the triethylene glycol with the jet stream of natural gas, all as hereinbefore set forth.

Operating pressures of the gas stream can vary between 10 PSI and 2000 PSI and the apparatus adjusted for operation at different pressures by interchangeable nozzles 17, each having a different sized jet opening 31. The triethylene glycol is injected at substantially 15 PSI in excess of the pressure of the gas stream.

It will thus be seen that the method and apparatus for separating water from a natural gas stream as disclosed herein provide an efficient means which will operate in freezing weather, that may be readily adjusted to varying volume and pressure changes in the natural gas stream, and that the apparatus and method work under pressure whereas the prior art devices operate at atmospheric pressure.

Although but one embodiment of the present invention has been illustrated and described, it will be apparent to those skilled in the art that various changes and modifications may be made therein without departing from the spirit of the invention and having thus described our invention what we claim is:

1. In an apparatus for drying a natural gas stream comprising interconnecting tubular members defining a generally horizontally extending continuous fluid flow path and a centrifugal separator tangentially connected at one end thereof, the improvement comprising an adapter conduit fluidly connected to one tubular member and having a first inner diameter at one end thereof, a nozzle chamber connected to said adapter at said first inner diameter, said nozzle chamber being adjacent the other end of said interconnected tubular members and means for introducing gas to be dried into said adapter conduit via said other end of said tubular members, a nozzle block removably positioned in said nozzle chamber and having a jet forming opening centrally thereof, said jet forming opening being connected directly to said adapter conduit and having a uniform inner diameter which is substantially smaller than said adapter conduit first inner diameter to define an orifice-like opening into which fluid from said adapter passes, said jet forming opening having an annular passageway separated therefrom, a diverging conduit fluidly connected to said orifice-like opening to receive fluid therefrom, and a plurality of individual nozzles positioned circumferentially in said nozzle block diverging conduit downstream of said orifice-like opening and communicating with said annular passageway, said nozzles being oriented to inject fluid into fluid flowing out of said orifice-like opening directed downstream toward an extension of an axial center line of said orifice-like opening, said nozzle block disposed in said nozzle chamber, an adjacent downstream portion of said interconnecting tubular members defining a mixing chamber which is fluidly connected to said diverging conduit and has an internal diameter essentially equal to the largest portion of said diverging conduit so that the area of said mixing chamber is substantially greater than the area of said orifice-like opening and means for supplying triethylene glycol under pressure greater than said gas stream to said annular passageway in said nozzle block for injection by said individual nozzles into the gas stream leaving said orifice-like opening.

2. The apparatus for drying a natural gas stream set forth in claim 1 and wherein the jet forming opening extends through the nozzle block at an apex of said diverging conduit.

3. The apparatus for drying a natural gas stream set forth in claim 1 and wherein said interconnecting tubular members are detachably connected to one another in the area thereof defining said nozzle chamber.

4. The apparatus for drying a natural gas stream set forth in claim 1 and wherein said means for supplying triethylene glycol to said annular chamber in said nozzle block comprises a pump and a glycol stripping station in communication with said annular chamber and said centrifugal separator.

5. The apparatus for drying a natural gas stream set forth in claim 1 and wherein said annular passageway has a portion thereof defining a conical chamber through which said gas stream is directed by said jet opening and wherein said individual nozzles are located in said portion forming said conical chamber.

* * * * *